(12) United States Patent
Röthl et al.

(10) Patent No.: US 8,288,145 B2
(45) Date of Patent: Oct. 16, 2012

(54) MEDIUM SUPPLEMENT FOR VIRUS PRODUCTION

(75) Inventors: Elisabeth Röthl, Vienna (AT); Andrej Egorov, Vienna (AT)

(73) Assignee: AVIR Green Hills Biotechnology, Vienna (AT)

( * ) Notice: Subject to any disclaimer, the term of this patent is extended or adjusted under 35 U.S.C. 154(b) by 0 days.

(21) Appl. No.: 12/444,248

(22) PCT Filed: Oct. 11, 2007

(86) PCT No.: PCT/EP2007/060804
§ 371 (c)(1),
(2), (4) Date: Apr. 3, 2009

(87) PCT Pub. No.: WO2008/043805
PCT Pub. Date: Apr. 17, 2008

(65) Prior Publication Data
US 2010/0003221 A1    Jan. 7, 2010

(30) Foreign Application Priority Data
Oct. 12, 2006  (EP) .................................. 06450142

(51) Int. Cl.
C12N 7/00 (2006.01)
C12N 7/02 (2006.01)
A61K 39/145 (2006.01)
A01N 63/00 (2006.01)

(52) U.S. Cl. .................. 435/235.1; 435/239; 424/93.6; 424/206.1

(58) Field of Classification Search ............... 435/235.1, 435/239; 424/93.6, 206.1
See application file for complete search history.

(56) References Cited

U.S. PATENT DOCUMENTS

| 4,783,411 | A * | 11/1988 | Gabliks .................... 435/237 |
| 5,958,423 | A * | 9/1999 | Chu ........................ 424/202.1 |
| 6,346,408 | B1 * | 2/2002 | Chueh ..................... 435/238 |
| 7,682,619 | B2 * | 3/2010 | Dubovi .................... 424/209.1 |
| 2003/0018074 | A1 * | 1/2003 | Kleiman et al. | |

FOREIGN PATENT DOCUMENTS

| EP | 1350510 B1 | 10/2003 |
| WO | WO 9738094 A1 | 10/1997 |
| WO | WO 9964068 A1 | 12/1999 |
| WO | WO 9964571 A1 | 12/1999 |
| WO | WO 0170239 A1 | 9/2001 |
| WO | WO 0224876 A1 | 3/2002 |
| WO | WO 2004110473 | 12/2004 |
| WO | WO/2008/006539 | 7/2007 |
| WO | WO 2008006539 | 7/2007 |

OTHER PUBLICATIONS

Shneider et al., 1981, Antibiotiki, vol. 26, No. 7, pp. 536-537, abstract.*
Govorkova et al., 1996, Journal of Virology, vol. 70, No. 8, p. 5519-5524.*
Kittel C et al: "Rescue of influenza virus expressing GFP from the NS1 reading frame" Virology, Academic Press,Orlando, US, vol. 324, No. 1, Jun. 20, 2004, pp. 67-73, XP004512673 ISSN: 0042-6822.
Frank et al., J. Clin Microb. 10:32-36, 1979.
Schepetink & Kok, J. Virol. Methods 42:241-250, 1993.
Nakamura et al., J Gen. Virol. 56:199-202, 1981.
Govorkova, EA et al., J. Virol. 1996, 70:5519-24.
Lau & Scholtissek, Virology 212:225-231, 1995.
Kaverin, NV and Webster, RG (J Virol. 1995, 69(4):2700-3.
Govorkova, EA et al., J. Infect. Dis. 1995, 172-250-3.
Borden, E et al., J.gen.Virol. 1979, 42, 297-303.
Borden, E et al., Archives of Virology, 1981, 69, 161-165.
Hamilton-Miller, JMT, Bacteriol. Reviews, 1973, 37, 166-196.
Chen, W. et al., Nat Med. 2001, 12:1306-12.
Zamarin, D, J. Virol. 2006, 80, 7976-7983.
Reed, LJ et al., 1938, Am. J. Hyg. 27:493-497.
Hoffmann E et al., ProcNatlAcadSci, 2002, 99:11411-6.
Hoffmann E et al., Vaccine, Aug. 19, 2002, 20(25-26): 3165-70.
Demidova et al., Vopr. Virosol, 346-352, 1979.
Grachev, Viral Vaccines, Mizrahi, ed., Wiley-Liss, New Yotrk 1990, pp. 39-67.
Romanova, J. et al., Virology, 2003, 307(1):90-97.
Romanova, J. et al., Virus Res 2004, 103:187-93.

* cited by examiner

Primary Examiner — Shin-lin Chen
(74) Attorney, Agent, or Firm — Michael Fedrick; Loza & Loza, LLP

(57) ABSTRACT

The use of macrolide polyene antibiotics or derivatives or analogues thereof as culture supplement for the propagation of virus is described. Further pharmaceutical compositions comprising a virus and a macrolide polyene antibiotic or a derivative or analogue thereof and methods for using of macrolide polyene antibiotics for transfection and infection of cells as well as the use of macrolide polyene antibiotics for the isolation of virus from clinical samples are disclosed.

14 Claims, 4 Drawing Sheets

Fig. 1c

MEDIUM SUPPLEMENT FOR VIRUS PRODUCTION

This application is the U.S. national stage of International Patent Application No. PCT/EP2007/060804, filed on Oct. 11, 2007 and entitled MEDIUM SUPPLEMENT FOR VIRUS PRODUCTION, which claims the benefit of priority from European Patent Application No. 06450142.2, filed on Oct. 12, 2006 and entitled MEDIUM SUPPLEMENT FOR VIRUS PRODUCTION. The disclosures of the foregoing applications are incorporated herein by reference in their entirety.

The present invention provides the use of a macrolide polyene antibiotic or a derivative or analogue thereof as culture supplement for the propagation of virus. Further a pharmaceutical composition comprising a virus and a macrolide polyene antibiotic or a derivative or analogue thereof and its use in cancer therapy and influenza treatment are described.

At present, many viral vaccines other than influenza are produced using primary trypsinized cells, for example cells from monkey kidneys, and the kidneys of rabbits and hamsters (see for example WO9738094). Primary diploid cell cultures have certain advantages such as easy preparation using simple media and bovine sera and sensitivity to a wide-range multiple viruses. However, primary diploid cells suffer from disadvantages, such as contamination by various adventitious agents, variable quality and sensitivity; and difficulty in obtaining suitable tissue for cultivation (e.g., monkey kidneys).

In contrast, the advantages of using continuous cell lines are their retention of native antigenic characteristics of the infected virus, standardization, high susceptibility to variants of the same virus, and ability to be grown as a large mass of cells using microcarrier or suspension fermentor systems.

However, these advantages themselves do make such cell lines suitable for use in vaccine production. Mizrahi, ed., Viral Vaccines, Wiley-Liss, New York (1990), pp. 39-67. For example, influenza A viruses isolated and passaged exclusively in mammalian cell cultures have been found in some cases to retain most or all of their original antigenic characteristics, a feature that would prove highly advantageous in vaccine production. (Romanova J. et al., Virology, 2003, 307 (1):90-7; Romanova J. et al., Virus Res. 2004, 103:187-93).

However, mammalian primary diploid cell cultures present difficulties as host systems for vaccine production. This is due to problems such as contamination of the cell culture with adventitious agents, variable quality of the cells in the cell culture, different sensitivities of the cells to variants of the same virus, low virus titers and the high cost and difficulties in obtaining and preparing such cell cultures.

Furthermore, only MDCK cells, among the continuous cell lines tested, have been reported to support potentially sufficient growth and isolation of viruses (Frank et al., J Clin. Microb. 10:3236 (1979); Schepetink & Kok, J Virol. Methods 42:241-250 (1993)).

Two other continuous cell lines—African green monkey kidney (Vero) cells and baby hamster kidney (BK-21)—are characterized, approved and certified by the World Health Organization (WHO) for production of human vaccines. However, Vero cells, while certified, were previously found unsuitable for large-scale production of human influenza virus vaccines. For example, the growth of influenza B in Vero cells was greatly restricted as compared to MDCK cells (Nakamura et al., J Gen. Virol. 56:199-202 (1981)). Additionally, attempts to use Vero cells to evaluate the rimantadine sensitivity of human H1N1 and H3N2 influenza A viruses gave ambiguous results, due to the low titers of viruses produced in these cells, as compared with MDCK cells (Gorvakova E A et al., J. Virol., 1996, 70:5519-24).

Thus, these and other studies indicate that influenza viruses have not previously replicated well in Vero cells, making them unsuitable for large-scale vaccine production. (Demidova et al., Vopr. Virosol (Russian) 346-352 (1979); Lau & Scholtissek, Virology 212:225-231 (1995)).

Kaverin N V and Webster R G (J. Virol., 1995, 69(4):2700-3) described the need of repeated addition of trypsin to the culture medium of influenza virus-infected Vero cells, restoring the multicycle growth pattern of influenza A virus strains. Yet the need of repeated addition of trypsin is quite laborious and time consuming as trypsin has to be added at various stages of cultivation (see also Gorvakova E A et al., J. Infect. Dis., 1995, 172:250-3).

Members of the family of DNA viruses contain double-stranded genomes. The family of parvoviridae is the lone exception. Most of the DNA genomes are not simply linear molecules. For example, papovavirus genomes are covalently closed, double-stranded circles, and hepadnavirus genomes are duplex circles in which one strand contains a nick and the other contains a gap. The ends of the double-stranded poxvirus genome are covalently joined, whereas herpesvirus genomes contain internal terminal and internal duplications.

DNA viruses are classified into following families: Parvoviridae, Papovaviridae, Adenoviridae, Hepadnaviridae, Herpesviridae, Iridoviridae, Bacuoloviridae and Poxviridae.

Double-stranded RNA viruses are classified into the two groups of Reoviridae and Birnaviridae.

Virus families containing enveloped single-stranded RNA of the negative-sense genome are classified into groups having non-segmented genomes (Paramyxoviridae, Rhabdoviridae, Filoviridae and Borna Disease Virus, Togaviridae) or those having segmented genomes (Orthomyxoviridae, Bunyaviridae and Arenaviridae). The Orthomyxoviridae family includes the viruses of influenza, types A, B and C viruses, as well as Thogoto and Dhori viruses and infectious salmon anemia virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode ten polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP).

Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo (U) sequences act as signals for the addition of poly (A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for eleven proteins: nine structural and nonstructural and the recently identified PB1-F2 protein.

In view of the difficulties for production of large amounts of virus particles needed for esp. prophylactic and therapeutic applications, it is an object of the invention to provide new cultivation methods and supplements that can increase the yield and quality of virus propagated in continuous cell lines.

The problem is solved by the use of a macrolide polyene antibiotic or a derivative or analogue thereof as culture supplement for the propagation of viruses. Preferably the macrolide polyene antibiotic is amphotericin B or a derivative or analogue thereof. According to prior art, macrolide polyenic antibiotics are known to show antifungal properties and are used extensively for the treatment and prevention of fungal infections in animals and human patients.

Besides the already known properties of macrolide polyenic antibiotics the inventors of the present invention have surprisingly shown that macrolide polyene antibiotics or a derivatives or analogues thereof can also be used for the cultivation and propagation of virus particles that are often difficult to be cultivated and which are needed in large amounts for various purposes like prophylactic, therapeutic and industrial applications. Amphotericin B methyl ester, a derivative of amphotericin B, was described to increase the infectivity of Enzephalomyocarditis virus RNA and SV40 virus DNA (Borden E. et al., J. gen. Virol., 1979, 42, 297-303; Borden E. et al., Archives of Virology, 1981, 69, 161-165) yet no prior art exists that showed or indicated its use for virus cultivation purposes.

Using the macrolide polyenic antibiotics and derivatives or analogues thereof according to the invention it is possible to increase virus growth, which might also result in increased infectivity of the virus particles even at low multiplicity of infection.

According to the invention, the viruses that can be successfully cultivated are DNA or RNA viruses, preferably they are RNA viruses, more preferably belonging to the families of Orthomyxoviridae, Picornaviridae and Paramyxoviridae. Even more preferred, the viruses are influenza A virus, influenza B virus, influenza C virus, rhinovirus and parainfluenzavirus and derivatives or analogues or fragments thereof. Alternatively, also measles virus, mumps virus, rubella virus and rabies virus can be useful systems for being cultivated according to the invention.

In an alternative embodiment, the viruses cultivated can contain modifications in several structural and non-structural genes, preferably modifications in the NS1 and/or PB1 genes. The modifications be deletions, substitutions or insertions of at least one nucleic acid.

Alternatively, the viruses cultivated by media containing macrolide polyene antibiotic or a derivative or analogue thereof can also be oncolytic viruses.

Virus derivatives, analogues or fragments can exemplarily be any virus particle that can still be used for vaccination purposes or show oncolytic capabilities.

The viruses are usually cultivated using virus infected cells that have been shown to be applicable for the purpose of propagating virus particles.

The invention also provides a method for the infection of cells for virus cultivation using macrolide polyene antibiotic or a derivative or analogue thereof wherein following steps are comprised:
a) cells are infected with at least one infectious virus particle
b) macrolide polyenic antibiotics and derivatives or analogues thereof are added to inoculum and/or cultivation media together with trypsin
c) incubation under appropriate conditions, followed by
d) harvesting of the virus yield and optionally
e) purification and/or characterization of the viruses.

Surprisingly it was shown that using the supplement or a mixture of supplements according to the invention there can be an increase of virus growth of at least 0.1 log 10, preferably at least 0.5 log 10, preferably 1 log 10, more preferred at least 2 log 10, even more preferred at least 2.5 log 10, even more preferred at least 5 log 10.

The present invention also provides a pharmaceutical formulation comprising a virus and a macrolide polyene antibiotic or derivative thereof. Preferably the virus is a live attenuated virus, alternatively according to the invention also whole inactivated virion, split or subunit vaccines are comprised.

According to an alternative embodiment, the pharmaceutical formulation can contain influenza virus and/or oncolytic virus together with a macrolide polyene antibiotic or a derivative or analogue thereof. According to the kind of virus used, the pharmaceutical preparation can be used for the treatment or prophylaxis of cancer or influenza infection.

Further the present invention can also be used for the isolation or titration of virus particles. This is particularly of importance as infection of cells for cultivation of virus often needs high amounts of virus due to lack of sufficient infection rates and inefficient replication mechanisms. The amount of virus can be highly reduced by adding at least one macrolide polyene antibiotic or a derivative or analogue thereof shortly prior or simultaneously or shortly after the infection process.

FIGURES

FIG. 1 shows the effect of amphotericin B in influenza virus growth Sub-confluent monolayer of Vero cells was at different multiplicity of infection moi (0.001, 0.0001 and 0.00001). Virus growth medium contained 5 µg/ml trypsin and 0 or 250 ng/ml amphotericin B. At each moi virus (with and w/o amphotericin B) was harvested when cytopathic effect of faster growing virus reached between 50 and 95%. For all viruses incubated in the presence of amphotericin B cytopathic effect and therefore virus titre developed faster than for those grown without amphotericin B. TCID50 titres were compared.

FIG. 1c shows the effect on influenza B strain.

a) Influenza B/Vienna/32/2006 (A/Malaysia/2506/2004-like) virus was titrated by plaque assay in presence (left column) and absence (right column) of amphotericin B. Virus grown in the presence of amphotericin B resulted in approx. 2.5 log increase of virus yield.

b) (A/New Caledonia/20/99 (H1N1)-like ΔNS1 virus is serially diluted and titrated in parallel in the presence and absence of 250 ng/ml amphotericin B by TCID50 assay. After 3 days incubation at 37° C. wells are evaluated for cytopathic effect and titres are calculated.

Figure 3:
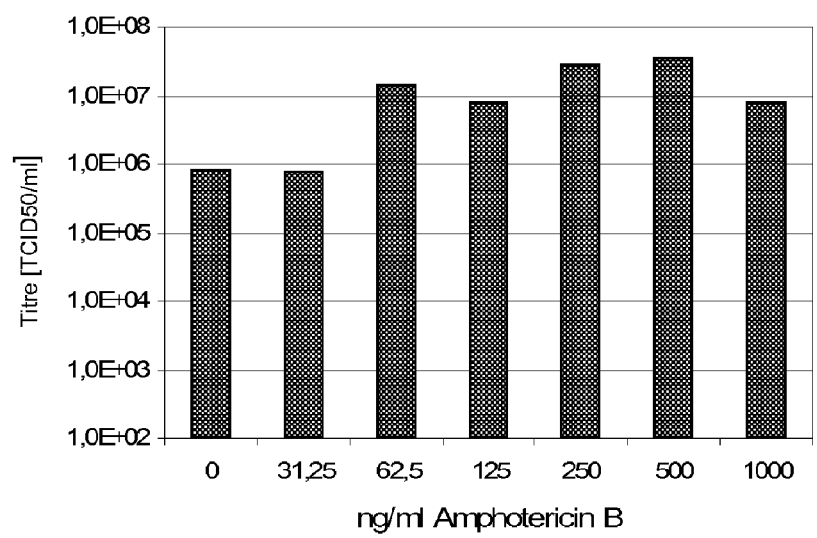

FIG. 3 shows dose escalation studies using amphotericin B.

Subconfluent monolayer of Vero cells was infected with A/Vienna/28/2006 (A/Wisconsin/67/2005-like) (H3N2) virus at multiplicity of infection of 0.001. After infection different concentrations of amphotericin B (0, 31.25, 62.5, 125, 250, 500 and 1000 ng/ml, respectively) were added to the growth medium. Virus was harvested after 48 hours and titrated by TCID50 assay in presence of amphotericin B. Use of concentrations in the range of 250 to 500 ng/ml resulted in highest virus titre.

Macrolide polyene antibiotics and derivatives and analogues thereof according to the invention can generally be divided into trienes, tetranes, pentanes, hexanes and heptanes according to the number of conjugated double bonds which they possess and according to the possession or lack of a glycosidically linked carbohydrate. For review, see Hamilton-Miller J. M. T., Bacteriol. Reviews, 1973, 37, 166-196. According to a preferred embodiment of the invention, the macrolide polyene antibiotics are heptanes, like for example amphotericin B, candidin, mycoheptin, X-63, candimycin, DJ400 B1, perimycin, antifungin 4915, eurotin A, heptane 757, monicamycin, neoheptane, Nystatin, Filipin, Primaricin, Natamycin and PA150 and derivatives and analogues thereof.

According to the most preferred embodiment, the macrolide polyene antibiotic is amphotericin B or a derivative or analogue thereof. Amphotericin B can be produced by cultivation of an organism like *Streptomyces nodosus* and extracted from the culture. Amphotericin B is essentially a high molecular weight macrocyclic lactone, possessing a chromophore of 7 conjugated double bonds. In addition to the large lactone nucleus, amphotericin B has other characteristic groups including an amino sugar. Derivatives or analogs thereof can be of any kind yet still providing the characteristics necessary for its use as cultivation supplement for the cultivation of viruses. Exemplary, it could be N-acetylation, N-succinylation, esterification, or complexing with $CaCl_2$. For example it can be an amphotericin B methyl ester or a liposomal formulation containing amphotericin B.

According to an alternative embodiment also mixtures of amphotericin B with its derivatives or various mixtures of amphotericin B derivatives can be used as supplement for virus cultivation and the methods according to the invention.

According to the invention macrolide polyene antibiotics and derivatives and analogues thereof are used in a concentration sufficient to promote the cultivation of viruses. Preferably the concentration is between 0.5 ng/ml and 5 microg/ml, preferably between 0.5 ng/ml and 2.5 microg/ml, preferably between 10 ng/ml and 900 ng/ml, more preferred between 100 ng/ml and 500 ng/ml, more preferred between 200 ng/ml and 400 ng/ml.

According to the present invention macrolide polyene antibiotics and derivatives and analogues thereof can be used for the cultivation of any DNA or RNA virus. In a preferred embodiment the virus is a RNA virus. Virus families containing enveloped single-stranded RNA of their negative-sense genome are classified into groups having non-segmented genomes (Paramyxoviridae, Rhabdoviridae, Filoviridae and Borna Disease Virus) or those having segmented genomes (Orthomyxoviridae, Bunyaviridae and Arenaviridae). The Orthomyxoviridae family includes the viruses of influenza, types A, B and C viruses, as well as Thogoto and Dhori viruses and infectious salmon anemia virus.

The genome of Orthomyxoviridae consists of six to eight single-stranded RNA molecules of negative polarity (complementary to mRNA). The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode ten polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP).

Exemplary, the viruses used for propagation or any methods as described here using the macrolide polyene antibiotics and derivatives and analogues thereof as culture supplements can be influenza virus, respiratory syncytial virus (RSV), Newcastle disease virus (NDV), vesicular stomatitis virus (VSV), rhinovirus and parainfluenza virus (PIV), measles and mumps virus, rubella virus and rabies virus.

The viruses used in the invention may be selected from naturally occurring strains, variants or mutants; mutagenized viruses (e.g., generated by exposure to mutagens, repeated passages and/or passage in non-permissive hosts); reassortants (in the case of segmented viral genomes); and/or genetically engineered viruses (e.g. using the "reverse genetics" techniques).

Preferably the virus cultivated by adding macrolide polyene antibiotics is selected from the group of influenza A, influenza B or influenza C virus.

According to the present invention the viruses can contain modifications within the genome leading to the expression and production of derivatives or analogues of the viruses. In an alternative embodiment the modification can be within the NS1 gene and/or the PB1 gene. This can lead to the production of a virus containing a fully deleted or otherwise modified NS1 protein and/or a fully deleted or modified PB1-F2 protein or modified PB2 protein expressed from the PB1 genomic fragment. The modifications within the NS1 gene can be deletions, insertions or substitutions. Examples for such modified RNA viruses are disclosed in WO99/64068 and WO99/64571 that are incorporated herein by reference, wherein the modifications within the NS1 gene lead to RNA viruses having an interferon antagonist phenotype that is responsible for attenuation.

The function of PB1-F2 has been described in detail by Chen W. et al., Nat Med. 2001, 12:1306-12. Modifications within the PB1-F2 protein which were shown to contribute to viral pathogenesis in mice have been described by Zamarin D. et al., J. Virol., 2006, 80, 7976-7983.

Alternatively the virus can also be an oncolytic virus. The major feature typical for oncolytic viruses is their conditionally replicating phenotype which permits them to grow in malignant cells but not in normal tissue. In a preferred embodiment of the invention it can be an oncolytic influenza A virus having a modification within the NS1 gene that does not grow in IFN-competent systems but replicate effectively in systems which lack expression of functional IFN.

The cells used for the cultivation of viruses using a cultivation medium that is supplemented by the macrolide polyene antibiotics or derivatives or analogues thereof can be any cells that can grow in vitro in synthetic media and can be used for the propagation of viruses. Within the scope of the invention, the term "cells" means the cultivation of individual cells, tissues, organs, insect cells, avian cells, mammalian cells, hybridoma cells, primary cells, continuous cell lines, and/or genetically engineered cells, such as recombinant cells expressing a virus. These can be for example BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells), chicken embryo cells or derivatives, embryonated egg cells, embryonated chicken eggs or derivatives thereof. Preferably the cell line is a VERO cell line.

The cultivation medium used for the production of viruses can be any medium known from prior art that is applicable for virus cultivation. Preferably the medium is a synthetic medium. This can be for example basal media as Modified Eagle's media MEM, minimum essential media MEM, Dulbecco's modified Eagle's media D-MEM, D-MEM-F12 media, William's E media, RPMI media and analogues and derivative thereof. These can also be specialty cell cultivation and virus growth media as VP-SFM, OptiPro™ SFM, AIM V® media, HyQ SFM4MegaVir™, EX-CELL™ Vero SFM, EPISERF, ProVero, any 293 or CHO media and analogues and derivatives thereof. These media can be supplemented by any additive known from prior art that is applicable for cell and virus cultivation as for example animal sera and fractions or analogues thereof, amino acids, growth factors, hormones, buffers, trace elements, trypsin, sodium pyruvate, vitamins, L-glutamine and biological buffers. Preferable medium is OptiPRO™ SFM supplemented with L-glutamine and trypsin.

In particular the macrolide polyene antibiotics or derivatives or analogues can also be used for increasing the effectiveness of the infection rate. To increase infection of the cells, the cells are contacted simultaneously with virus particles and the macrolide polyene antibiotics or derivatives or analogues thereof. Alternatively the cells can be pretreated with the macrolide polyene antibiotics or derivatives or analogues thereof shortly before, simultaneously or shortly after the virus particles are added to the cells. The preferred time range would therefore be between 1 hour before or after the infection, more preferred between 0.5 hours before or after the infection.

It is well known from prior art that high multiplicity of infection (MOI) results in the production of a high number of defective virus particles that show decreased or no infectivity. It can therefore be advantageous for economical and scientific reasons to provide means where low (MOI of 0.001) or even better very low MOI (MOI of 0.0001 up to 0.00001) or even lower MOI can be used for infection of cells.

Using the supplement or a mixture of supplements according to the invention there can be an increase of virus growth of at least 0.1 log 10, at least 0.5 log 10, preferably at least 1 log 10, more preferred at least 2 log 10, even more preferred at least 2.5 log 10, even more preferred at least 5 log 10.

A further embodiment of the invention is the use of a macrolide polyene antibiotic or a derivative or analogue thereof for the transfection of Vero cells with expression plasmids coding for viral RNA segments. Again, a macrolide polyene antibiotic is added to the cultivation medium shortly before, simultaneously or shortly after the cells that were transfected with expression plasmids containing all or part of the viral complete genome.

A further embodiment of the invention provides a pharmaceutical formulation comprising live attenuated or inactivated virus and a macrolide polyene antibiotic or derivative thereof optionally together with a pharmaceutically acceptable carrier. Preferably the virus is an influenza virus and/or an oncolytic virus.

In case the pharmaceutical preparation comprises an oncolytic virus, it can be used for viral cancer therapy. In case the pharmaceutical preparation comprises an influenza virus it can be used for the treatment of influenza virus infection.

Preferably, the pharmaceutical preparation comprises a live attenuated virus, but also inactivated or other viruses can be used.

The preparation can be administered in a suitable amount. A suitable amount could be in the range of 2 to 10 logs, preferred 5 to 9 logs, more preferred of 6.5 to 8 logs of virus particle.

The preparation used according to the invention preferably is provided in a suitable formulation. Preferred are such formulations with a pharmaceutically acceptable carrier.

The latter comprises, e.g., auxiliary agents, buffers, salts and preservatives. Preferably, a ready to use infusion solution is provided. Since a virus preparation is relatively stable, medicaments based on viruses or their derivatives have the substantial advantage that they can be put on the market as a storage-stable solution, or as a formulation in a ready-to-use form. The former preferably is storage-stable in the formulation at refrigerator temperatures up to room temperature. The preparation used according to the invention may, however, also be provided in frozen or lyophilized form which may be thawed or reconstituted when required. Usually, the preparation will be administered intranasally or intramuscularly. Likewise, however, also another parenteral or mucosal mode of administration can be chosen, which brings the active substance to a systemic or local application at the site of infection or tumour.

The present invention also provides means to speed up and increase the quality and sensitivity of standard TCID50, TCID50-based or plaque assays. According to the use of the macrolide polyene antibiotics for cultivation of virus the growth of virus is accelerated and therefore the assays can be analyzed earlier and a more accurate titration result can be achieved at an earlier time point.

Moreover the present invention provides a method for the isolation of virus from clinical samples wherein cells, for example Vero cells, are infected with virus particles from the patient's respiratory tract in the presence of a macrolide polyene antibiotic or derivative or analogue thereof, infected cells are incubated under appropriate conditions to promote virus growth in the presence of a macrolide polyene antibiotic or derivative or analogue thereof and isolation and characterization of the virus.

Influenza virus surveillance programs require efficient systems for isolation of influenza viruses from clinical specimens. Usually this procedure includes infection of embryonated chicken eggs or MDCK cells with material taken from the nasal-throat washings. Efficacy of the procedure varies from year to year depending on a type of a virus and cell substrate. It is known that isolation in eggs and some times also in MDCK can generate mutated virus variants distinct from the real viruses circulating in human population. It was shown that Vero cells could be a better substrate for influenza virus isolation and characterization since properties of Vero derived viruses are more closely reflect the nature of human viruses (Romanova J., et al. 2003). At the same time, unfortunately, the sensitivity of Vero cell line for virus isolation is lower than on MDCK cells.

According to the invention amphotericin B improves influenza virus isolation from clinical samples in Vero cells. Using the method according to the invention increase of percentage of positive isolation cases can be provided as usually the virus is very difficult to be re-isolated from clinical specimens in Vero cells.

The foregoing description will be more fully understood with reference to the following examples. Such examples are, however, merely representative of methods of practicing one or more embodiments of the present invention and should not be read as limiting the scope of invention.

EXAMPLES

Example 1

The target of this experiment is to determine the effect of amphotericin B on various influenza viruses at decreasing multiplicity of infection. The three viruses chosen are reflecting the currently circulating subtypes of H1N1, H3N2 and B, as also recommended by WHO for seasonal vaccine 2006/07 in northern hemisphere. (http://www.who.int/csr/disease/influenza/vaccinerecommendations1/en/).

Subconfluent monolayer of serum-free Vero cells is infected with decreasing multiplicity of infection, of 0.001, 0.0001 or 0.00001. Two representative Influenza A viruses, A/New Caledonia/20/99 (H1N1) and A/Vienna/28/2006 (H3N2) (A/Wisconsin/67/2005-like) as well as one candidate of influenza B, B/Vienna/32/2006 (B/Malaysia/2506/2004-like), is used. Growth medium added after infection is supplemented with 5 μg/ml trypsin as well as 0 or 250 ng/ml amphotericin B, respectively. Supernatant of all cells infected with the same multiplicity of infection (0 and 250 ng/ml amphotericin B) is harvested when a cytopathic effect of 50% or more is observed on faster growing virus. Virus titres are determined by TCID50 assay.

Figure 1A:
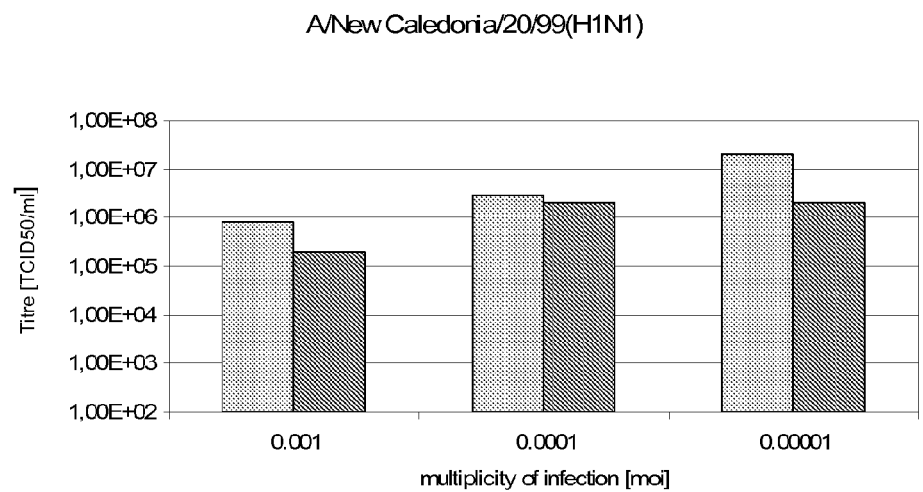
FIG. 1a shows the effect on H1N1 strain.
Figure 1B:
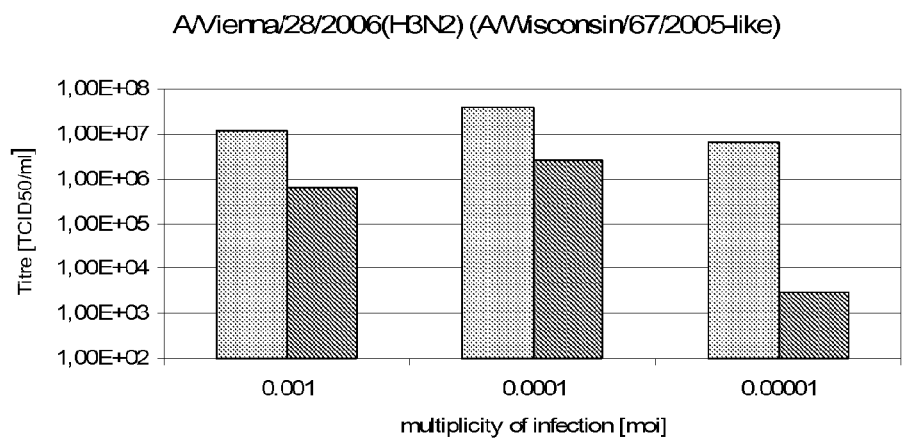
FIG. 1b shows the effect on H3N2 strain.
Figure 1C:
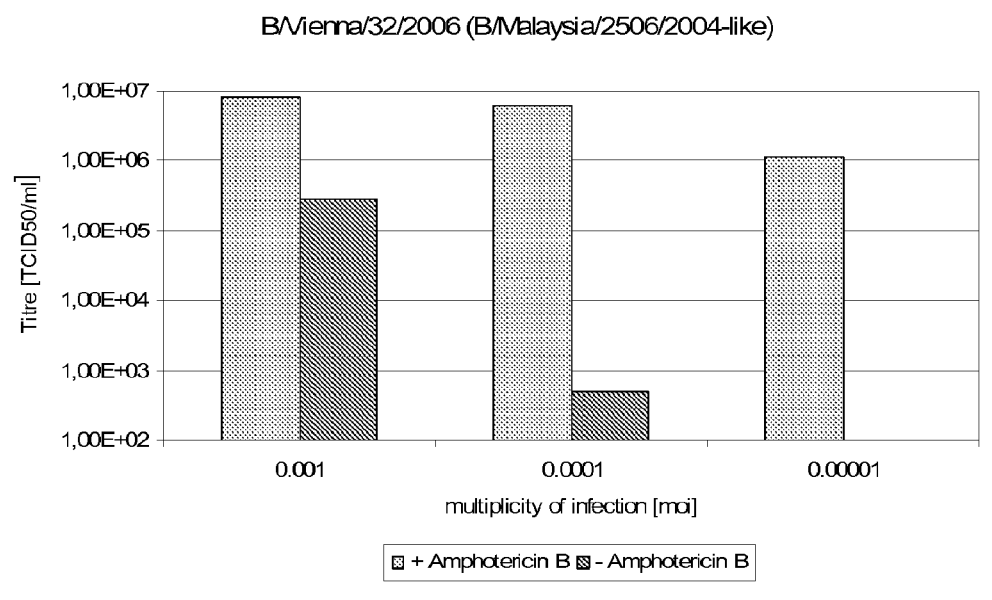

As illustrated in FIGS. 1a, 1b and 1c for all three viruses tested a positive effect of amphotericin B on virus replication can be concluded. For A/New Caledonia/20/99 (H1N1) an effect of amphotericin B on virus growth can be observed. In the presence of amphotericin B titres range from 8E+05 to 2E+07 TCID50/ml with decreasing moi (multiplicity of infection), at the lowest moi, 1 log less virus is obtained when no amphotericin B is added. In the case of A/New Caledonia/20/99 the lowest moi of 0.00001 seems to be the most optimal in terms of virus growth and effect of amphotericin B.

A/Vienna/28/2006 (H3N2) virus confirms the results of the H1N1 virus showing even greater sensitivity to the effect of the substance. At all three tested moi's a minimum of 1 log higher virus titre less is obtained if grown in the presence of amphotericin B and harvested at the same timepoint.

An even more striking effect of the substance is observed for the B/Vienna/32/2006 (B/Malaysia/2506/2004-like) virus. Titres measured for virus grown in the presence of amphotericin range from 1.E+07 (moi 0.001) to 1 E+06 (moi 0.00001) TCID50/ml. In contrast when no amphotericin is added virus hardly replicates leading to titres below 3E+05 TCID50/ml, for the lowest moi no virus at all is obtained. Compared to the A viruses the B virus shows the greatest sensitivity to the substance. This can partially be explained by the fact that it was adapted to growth on serum-free Vero cells in the presence of amphotericin B.

In general it can be concluded that there is a clear effect of amphotericin B on virus growth of all three above discussed virus subtypes.

Material and Methods:
Cells and Viruses:
Vero cells are cultivated in serum-free conditions, medium used is OptiPro™ SFM supplemented with 4 mM L-glutamine. Cells are cultivated by passaging every 2 to 3 days in ratio of 1:3 to 1:4. Growth medium used is SFM supplemented with 4 mM L-glutamine.

A/New Caledonia/20/99 is derived from NIBSC, product number 03/208, and is passaged 3 times on MDCK cells. Adaptation to growth on serum-free Vero cells is done by passaging of MDCK-derived virus 4 times in Vero cells in the absence of amphotericin B.

A/Vienna/28/2006 (H3N2) and a A/Wisconsin/67/2005 (H3N2)-like virus was isolated from a clinical specimen and is passaged 1 time on MDCK cells followed by 5 passages on serum-free Vero cells in the presence and then absence of amphotericin B.

B/Vienna/32/2006, a B/Malaysia/2506/2004-like virus, was isolated from a clinical specimen in MDCK cells (2 passages) and then adapted to growth on serum free Vero cells passaging 6 times in the presence of amphotericin B.

Potency Assay

Titration of viruses was done by TCID50 (tissue culture infectious dose) assay, a cell based assay allowing statistical determination of virus potency in 96-well plates. The virus is serially diluted, subconfluent monolayer of Vero cells (96-well plate) is infected, virus is grown in the presence of 5 μg/ml trypsin and 250 ng/ml amphotericin B at 33° C. (B virus) and 37° C. (A virus). After 3 to 6 day incubation wells are checked for cytopathic effect and titre is calculated based on the formula by Reed L. J. et al., 1938, Am. J. Hyg. 27:493-497.

Example 2

A B virus (B/Malaysia/2506/2004-like) and an A/H1N1 virus (A/New Caledonia/20/99 (H1N1)-like ΔNS1) are titrated by two different methods in the presence and absence of amphotericin B. In both cases a clear effect of the substance on the final virus titre can be observed as illustrated in FIGS. 2a and b.

Figure 2A:
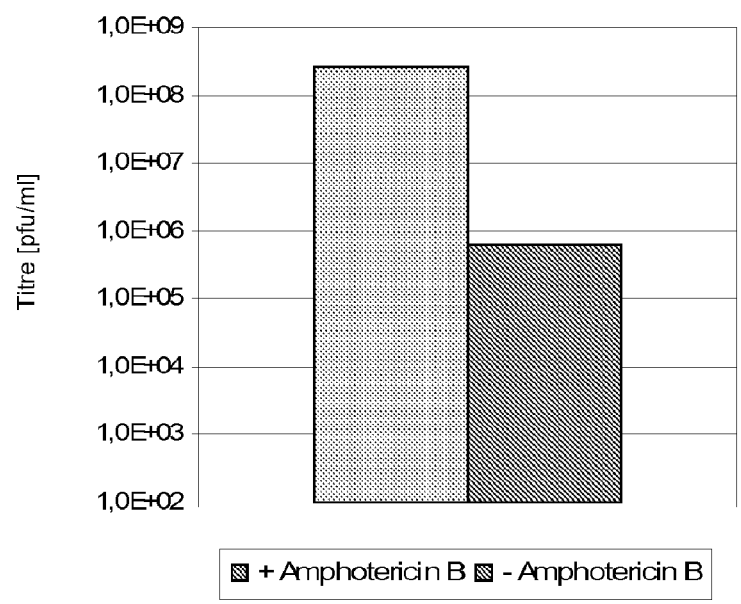
FIG. 2 shows the results of titration in the presence and absence of amphotericin B.

In FIG. 2a B/Vienna/32/2006 (B/Malaysia/2506/2004-like) virus is serially diluted and titrated in parallel in the presence and absence of 250 ng/ml amphotericin by plaque assay. After 5 days incubation at 33° C. plaques are counted and their number is directly compared.

Figure 2B:
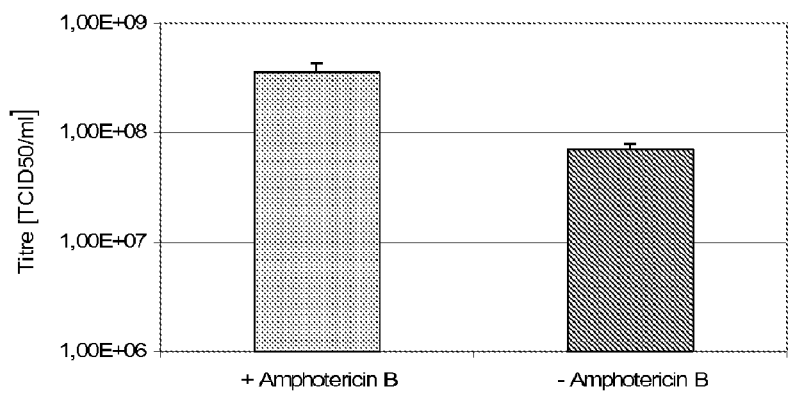

In FIG. 2b (A/New Caledonia/20/99 (H1N1)-like ΔNS1 virus is serially diluted and titrated in parallel in the presence and absence of 250 ng/ml Amphotericin B by TCID50 assay. After 3 days incubation at 37° C. wells are evaluated for cytopathic effect and titres are calculated.

As can be seen in FIG. 2a a more than 2 log higher titre is obtained when the same virus is grown in the presence of amphotericin B. In the presence of amphotericin B more than 1E+08 pfu/ml titre of B virus is reached. This result shows clearly that sensitivity of the plaques assay is significantly increased by addition of the substance.

In FIG. 2b A/H1N1 virus titrated by TCID50 in the presence and absence of Amphotericin B. Also here a significant increase of titre is observed, a nearly 1 log increase of sensitivity is achieved.

Material and Methods:
Cells and Viruses:
Vero cells are cultivated in serum-free conditions, medium used is OptiPro™ SFM supplemented with 4 mM L-glutamine. Cells are cultivated by passaging every 2 to 3 days in ratio of 1:3 to 1:4 at 37° C., 5% $CO_2$.

B/Vienna/32/2006 is derived from a B/Malaysia/2506/2004-like clinical isolate, isolated in MDCK cells (2 passages) and then adapted to growth on serum free Vero cells passaging 6 times in the presence of amphotericin B at 33° C.

A/New Caledonia/20/99 (H1N1)-like ΔNS1 virus contains surface proteins HA and NA from A/New Caledonia/20/99 (H1N1) virus and internal segments from A/Puerto Rico/8/

34, whereas part of the NS (Non Structural) segment is deleted. This virus was generated by reverse genetics and passaged on Vero cells in the absence of Amphotericin B at 37° C.

Potency Assay

Plaque Assay

Titration of virus is done by plaque assay. Virus is serially diluted, confluent monolayer of Vero cells is infected, overlay is consisting of Vero growth medium supplemented with 0.01% DEAE Dextrane, 10×DMEM, saturated sodiumhydrogencarbonate, 5 μg/ml trypsin and 0 or 250 ng amphotericin B.

TCID50 Assay

TCID50 (tissue culture infectious dose) assay is a cell based assay allowing statistical determination of virus potency in 96-well plates. The virus is serially diluted, subconfluent monolayer of Vero cells (96-well plate) is infected, virus is grown in the presence of 5 μg/ml trypsin and in the presence or absence of 250 ng/ml amphotericin B at 37° C. After a 3 day incubation period wells are checked for cytopathic effect and titre is calculated based on the formula by Reed L. J. et al., 1938, Am. J. Hyg. 27:493-497.

Example 3

In this experiment different doses of amphotericin B are added after infection of Vero cells by an A/Wisconsin/67/2005 (H3N2)-like virus. By increasing the concentration of amphotericin B virus replication can be enhanced, concentrations between 62.5 and 1000 ng/ml show a clear effect.

Subconfluent monolayer of serum-free Vero cells is infected by A/Vienna/28/2006 (H3N2) an A/Wisconsin/67/2005-like virus at a multiplicity of infection of 0.001. Virus is grown in the presence of different concentrations of amphotericin B, namely 0, 31.25, 62.5, 125, 250, 500 and 1000 ng/ml. Virus is harvested after 48 hours and titrated by TCID50 assay in the presence of 250 ng/ml amphotericin B.

Titres were obtained in the range from 8E+05 to 4E+07 TCID50/ml. At the two lowest concentrations (0 and 31.25 ng/ml) virus titres are below 1 E+06 TCID50/ml whereas virus titre is increasing to above 3E+07 TCID50/ml at 250 and 500 ng/ml amphotericin B. For illustration of results see FIG. 3.

Material and Methods:

Cells and Viruses:

Vero cells are cultivated in serum-free conditions, medium used is OptiPro™ SFM supplemented with 4 mM L-glutamine. Cells are cultivated by passaging every 2 to 3 days in ratio of 1:3 to 1:4 at 37° C., 5% $CO_2$.

A/Vienna/28/2006 (H3N2), an A/Wisconsin/67/2005 (H3N2)-like virus isolated derived from a clinical specimen is passaged 1 time on MDCK cells followed by 5 passages on serum-free Vero cells in the presence and then absence of amphotericin B.

Potency Assay

Titration of viruses is done by TCID50 (tissue culture infectious dose) assay, a cell based assay allowing statistical determination of virus potency in 96-well plates. The virus is serially diluted, subconfluent monolayer of Vero cells (96-well plate) is infected, virus is grown in the presence of 5 μg/ml trypsin and 250 ng/ml amphotericin B at 33° C. (B virus) and 37° C. (A virus). After 3 to 6 day incubation wells are checked for cytopathic effect and titre is calculated based on the formula by Reed L. J. et al., 1938, Am. J. Hyg. 27:493-497.

Example 4

Use of amphotericin B for efficient rescue of virus after transfection In this example serum-free Vero cells are transfected with 8 plasmids encoding the 8 segments of A/Wisconsin/67/2005 (H3N2)-like virus as described by Hoffman et al., including several modifications (Hoffmann E. et al., Proc Natl Acad Sci, 2002, 99:11411-6). Growth medium containing 250 ng/ml amphotericin B and 5 μg/ml trypsin is added 6 hours later. Virus is partially harvested 6 days after transfection when clear cytopathic effect of transfectant virus grown the in the presence of amphotericin B is observed and signs of cytopathic effect are also visible in the absence of amphotericin B. Virus without amphotericin B is further monitored another 3 days not showing any signs that cytopathic effect is progressing. Titre is determined by TCID50 assay in presence of 250 ng/ml amphotericin B.

As illustrated in table 1 a titre of 2E+04 TCID50/ml is obtained in the presence of Amphotericin B whereas no virus is detectable in its absence.

This example clearly indicates that virus which would otherwise not grow can be efficiently rescued in the presence of amphotericin B only.

Material and Methods:

Cells and Viruses:

Vero cells are cultivated in serum-free conditions, medium used is OptiPro™ SFM supplemented with 4 mM L-glutamine. Cells are cultivated by passaging every 2 to 3 days in ratio of 1:3 to 1:4 at 37° C., 5% $CO_2$.

A/Vienna/28/2006 (H3N2) is a A/Wisconsin/67/2005 (H3N2)-like virus derived from a clinical specimen that is passaged 1 time on MDCK cells followed by 5 passages on serum-free Vero cells in the presence and then absence of Amphotericin B. Segments of the virus are cloned into plasmids which enable at the same time transcription of viral RNA as template for genome as well as mRNA for further processing to viral protein (Hoffmann et al; Eight-plasmid system for the rapid generation of influenza virus vaccines, Vaccine (20). 2002), wherein the plasmids were modified accordingly. All 8 plasmids are transfected into Vero cells by electroporation. Six hours after transfection serum-free medium containing 5 μg/ml trypsin as well as 0 and 250 ng/ml amphotericin B, respectively, is added. Transfectant virus is partially harvested after 6 days and further observed for another 3 days.

Potency Assay

Titration of viruses was done by TCID50 (tissue culture infectious dose) assay, a cell based assay allowing statistical determination of virus potency in 96-well plates. The virus is serially diluted, subconfluent monolayer of Vero cells (96-well plate) is infected, virus is grown in the presence of 5 μg/ml trypsin and 250 ng/ml amphotericin B at 33° C. (B virus) and 37° C. (A virus). After up to 6 day incubation period wells are checked for cytopathic effect and titre is calculated based on the formula by Reed L. J. et al., 1938, Am. J. Hyg. 27:493-497.

| addition of Amphotericin B [+/−] | titre [TCID50/ml] |
|---|---|
| + | 2.0E+04 |
| − | <1.0E+01 |

Example 5

Virus Isolation from Clinical Samples in Vero Cells Using Amphotericin B 9 clinical samples from the patients with confirmed influenza B virus infection were evaluated for the frequency of virus isolation on Vero cells in the presence or absence of amphotericin B. Only viruses from 3 specimens were successfully isolated when amphotericin B was not added. At the same time all 9 probes were positive in case when 500 ng/ml of amphotericin B was added into maintenance medium.

The invention claimed is:

1. A method of propagating influenza virus, comprising the step of adding amphotericin B to a cell culture comprising VERO cells and the influenza virus.

2. The method of claim 1, wherein the amphotericin B is added to the cell culture at a concentration of between 0.5 ng/ml and 5 microg/ml.

3. The method of claim 2, wherein the amphotericin B is at a concentration of between 0.5 ng/ml and 2.5 µg/ml.

4. The method of claim 3, wherein the amphotericin B is at a concentration of between 10 ng/ml and 900 ng/ml.

5. The method of claim 4, wherein the amphotericin B is at a concentration of between 100 ng/ml and 500 ng/ml.

6. The method of claim 5, wherein the amphotericin B is at a concentration of between 200 ng/ml and 400 ng/ml.

7. The method of claim 1, wherein the influenza virus is selected from the group consisting of influenza A virus, influenza B virus, and influenza C virus.

8. The method of claim 1, wherein the influenza virus contains a modification within the NS1 or PB1 gene.

9. The method of claim 8, wherein the modification is a deletion, substitution or insertion of at least one nucleic acid.

10. The method of claim 1 wherein virus growth in the cell culture is increased compared to virus growth in the absence of amphotericin B by an amount of at least 0.1 log 10, preferably at least 0.5 log 10, more preferably at least 1 log 10, more preferably at least 2 log 10, and even more preferably at least 2.5 log 10.

11. A method of transfecting Vero cells, comprising the step of adding amphotericin B to a cell culture comprising Vero cells before, simultaneously with or shortly after transfecting the Vero cells with expression plasmids containing viral RNA segments of influenza virus.

12. A method for the infection of cells for influenza virus cultivation using amphotericin B, comprising the following steps:
 a) infecting cells with at least one infectious influenza virus particle;
 b) adding at least amphotericin B to an inoculum or cultivation media together with trypsin to form a cell culture mixture;
 c) incubating the cells with the cell culture mixture; followed by
 d) harvesting of influenza viruses.

13. The method of claim 12, further comprising the step of purifying the harvested virus.

14. The method of claim 12, further comprising the step of characterizing the harvested virus.

* * * * *